United States Patent
Li et al.

(10) Patent No.: US 11,781,068 B2
(45) Date of Patent: Oct. 10, 2023

(54) CORROSION INHIBITOR FOR SOFT WATER CIRCULATION HEATING AND COOLING SYSTEM AND PREPARATION METHOD OF CORROSION INHIBITOR

(71) Applicants: Shanghai CEO Environmental Protection Technology Co., Ltd., Shanghai (CN); Tongji University, Shanghai (CN)

(72) Inventors: Fengting Li, Shanghai (CN); Yufei Lu, Shanghai (CN); Bingru Zhang, Shanghai (CN); Xianwei Qu, Shanghai (CN); Chunjiang Li, Shanghai (CN)

(73) Assignees: Shanghai CEO Environmental Protection Technology Co., Ltd., Shanghai (CN); Tongji University, Shanghai (CN)

( * ) Notice: Subject to any disclaimer, the term of this patent is extended or adjusted under 35 U.S.C. 154(b) by 554 days.

(21) Appl. No.: 17/005,322

(22) Filed: Aug. 28, 2020

(65) Prior Publication Data

US 2020/0392407 A1    Dec. 17, 2020

(30) Foreign Application Priority Data

Dec. 2, 2019   (CN) .......................... 201911214441.0

(51) Int. Cl.
| | | |
|---|---|---|
| *C09F 5/12* | (2006.01) | |
| *C09K 15/28* | (2006.01) | |
| *C02F 5/12* | (2023.01) | |
| *C07C 335/32* | (2006.01) | |
| *C23F 11/16* | (2006.01) | |
| *C02F 103/02* | (2006.01) | |

(52) U.S. Cl.
CPC ................ *C09K 15/28* (2013.01); *C02F 5/12* (2013.01); *C07C 335/32* (2013.01); *C23F 11/16* (2013.01); *C02F 2103/023* (2013.01)

(58) Field of Classification Search
CPC ...... C09K 15/28; C02F 5/12; C02F 2103/023; C07C 335/32; C23F 11/16
See application file for complete search history.

(56) References Cited

U.S. PATENT DOCUMENTS

| | | | | |
|---|---|---|---|---|
| 2012/0101041 A1* | 4/2012 | Mynar | ................. | C08G 65/331 426/573 |
| 2014/0224495 A1* | 8/2014 | Khandekar | ............ | C09K 8/035 560/182 |
| 2015/0128484 A1* | 5/2015 | Nordvik | .................. | C07C 69/84 554/1 |
| 2015/0252246 A1* | 9/2015 | Fossen | .................... | C10L 3/107 560/180 |
| 2017/0182193 A1* | 6/2017 | Licha | ................. | A61K 49/0032 |
| 2017/0306101 A1* | 10/2017 | Shen | .................... | C08G 83/006 |
| 2020/0377691 A1* | 12/2020 | Zhen | ..................... | B60C 1/0016 |
| 2021/0395898 A1* | 12/2021 | Ul-haq | ................. | C23F 11/173 |

FOREIGN PATENT DOCUMENTS

| | | | | |
|---|---|---|---|---|
| CN | 106277376 A | * | 1/2017 | ................ C02F 5/12 |
| CN | 106431906 A | * | 2/2017 | ............. C07C 67/08 |

OTHER PUBLICATIONS

English translation of CN 106277376A, 5 pages (Year: 2023).*
English translation of CN 106431906A, 5 pages (Year: 2023).*

* cited by examiner

*Primary Examiner* — Alicia Bland

(57) ABSTRACT

A corrosion inhibitor for a soft water circulation heating and cooling system, wherein the corrosion inhibitor is pentapentanol core hyperbranched macromolecule functionalized by isothiourea and carboxyl, which has a chemical formula of $C_5H_7O_5\{COC(CH_3)[CH_2OCOCH_2CH(COOH)SC(NH)NH_2]_2\}_5$. The corrosion inhibitor provided by the present invention is non-phosphorus, biodegradable, non-toxic, low in cost and has good corrosion inhibition effect. Moreover, it has excellent corrosion inhibition performance for circulating heating and cooling systems using soft water as the water source, and can significantly improve the reuse rate of circulating water. The present invention also provides a preparation method of the corrosion inhibitor, which is simple, easy to obtain raw materials and easy to industrialize.

5 Claims, No Drawings

CORROSION INHIBITOR FOR SOFT WATER CIRCULATION HEATING AND COOLING SYSTEM AND PREPARATION METHOD OF CORROSION INHIBITOR

CROSS REFERENCE OF RELATED APPLICATION

The present invention claims priority under 35 U.S.C. 119(a-d) to CN 201911214441.0, filed Dec. 2, 2019.

BACKGROUND OF THE PRESENT INVENTION

Field of Invention

The present invention relates to the field of industrial water treatment system and chemical technology, and more particularly to a corrosion inhibitor for a soft water circulation heating and cooling system and a preparation method of the corrosion inhibitor.

Description of Related Arts

In the industrial field, cooling water and heating (or heat preservation) water are often recycled and operated at a high concentration ratio for saving water. However, with the increase of the concentration ratio, scaling (such as calcium carbonate, calcium sulfate and barium sulfate) inevitably becomes more and more serious. At the same time, the problems of bacterial growth and under-scale corrosion are also more prominent, which hinders the increase of the concentration ratio and makes it difficult to save water. Therefore, in recent years, one of the important measures to save circulating water is to use soft water without calcium ions as the water source and supplementary water of the water circulation system.

In some industries, since the cooled device is special or the medium is high in temperature, it is often necessary to use the soft water as the water source of circulating cooling water; after being cooled through the cooling tower, the soft water continuously cyclically runs, such as the circulating cooling water for continuous casting mold in steel industry, the circulating cooling water for nuclear power generation system, the circulating cooling water for oxygen lance in metallurgical industry, the circulating cooling water for float glass production line and the circulating cooling water for central air-conditioning system. In addition, some industries require insulation or heating, so it is often necessary to use the soft water as the water source of circulating hot water; after being heated by the atmospheric boiler, the soft water continuously cyclically runs, such as the chemical reaction system which require heating, and plate-and-frame filter press system of sludge dewatering and drying which be maintained at a range of 60 to 95° C.

The soft water has a very low calcium ion concentration or contains almost no calcium ions, its water quality is acidic with a pH value in a range of 5 to 7, and its electrical conductivity is extremely low ($\leq 2.0$ μs·cm$^{-1}$). The remarkable characteristics of this kind of water are that it has no scaling and is acidic. Because there is no protection of scaling layer, the dissolved oxygen in the soft water directly contacts with the metal, showing strong corrosiveness. In the past, the soft water is subjected to corrosion inhibition treatment with high-concentration chromate or nitrite. Although this method has a good treatment effect, chromate and nitrite are carcinogens, which cause serious environmental pollution and have been banned.

Traditional corrosion inhibitors include metal salt corrosion inhibitors (such as molybdate and tungstate), silicate corrosion inhibitors, and organic phosphine corrosion inhibitors. Molybdate and tungstate are precious metal salts. Although they are able to be used for corrosion inhibition of soft water systems and are non-toxic, they are large in consumption (even as high as 1500 mg·L$^{-1}$), and high in cost. Silicate is a kind of precipitation film-type corrosion inhibitor, and is able to be used for corrosion inhibition of soft water systems. It is cheap and non-toxic, and however, when its dosage is insufficient, pitting corrosion is likely to occur, and if its dosage is too large, colloidal silica scaling that is difficult to be cleaned is easy to produce. Through combining with a small amount of calcium ions, organic phosphine corrosion inhibitors are adsorbed on the surface of carbon steel or stainless steel to exert the corrosion inhibition effect. Therefore, organic phosphine corrosion inhibitors are basically ineffective for the corrosion inhibition of the soft water system with extremely low calcium content or even without calcium ions. Moreover, due to containing phosphorus, organic phosphine corrosion inhibitors also easily lead to eutrophication.

At present, the development of environmentally friendly phosphorus-free corrosion inhibitors at home and abroad is mainly based on long-chain fatty amines and imidazoline corrosion inhibitors, as well as natural amino acids and thiocarboxylic acid corrosion inhibitors. These types of corrosion inhibitors are able to inhibit the corrosion of metals in oilfield reinjection water and open circulating cooling water systems to a certain extent, but they are unable to solve the corrosion problem of carbon steel in soft water closed circulation heating and cooling systems. The cost of this kind of phosphorus-free corrosion inhibitor is higher than that of traditional organic phosphine corrosion inhibitor, which further hinders its large-scale application in actual production.

SUMMARY OF THE PRESENT INVENTION

An object of the present invention is to provide a corrosion inhibitor that is phosphorus-free, biodegradable, non-toxic, environmentally friendly, low in cost, and has a good corrosion inhibition effect on a circulation heating and cooling system which uses soft water as circulating water.

To achieve the above object, the present invention provides a corrosion inhibitor for a soft water circulation heating and cooling system, wherein the corrosion inhibitor is pentapentanol core hyperbranched macromolecule functionalized by isothiourea and carboxyl, which takes isothiourea and carboxyl as functional end groups, and takes pentapentanol as a core, has a chemical formula of $C_5H_7O_5\{COC(CH_3)[CH_2OCOCH_2CH(COOH)SC(NH)NH_2]_2\}_5$, and a structural formula of:

(Formula 1)

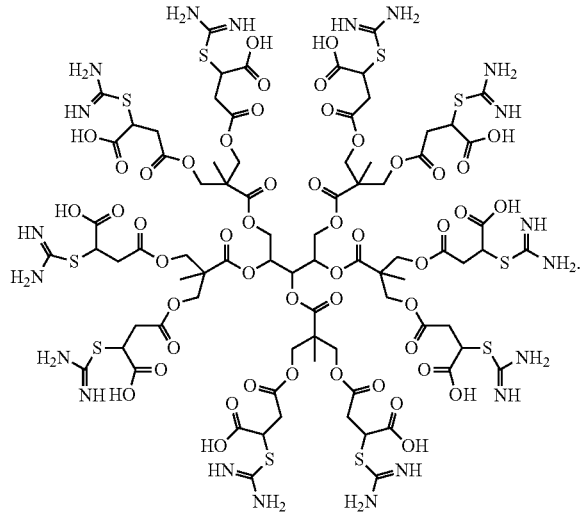 [SMILES: CC(COC(=O)CC(SC(=N)N)C(=O)O)(COC(=O)CC(SC(=N)N)C(=O)O)C(=O)OCC(OC(=O)C(C)(COC(=O)CC(SC(=N)N)C(=O)O)COC(=O)CC(SC(=N)N)C(=O)O)C(OC(=O)C(C)(COC(=O)CC(SC(=N)N)C(=O)O)COC(=O)CC(SC(=N)N)C(=O)O)C(COC(=O)C(C)(COC(=O)CC(SC(=N)N)C(=O)O)COC(=O)CC(SC(=N)N)C(=O)O)OC(=O)C(C)(COC(=O)CC(SC(=N)N)C(=O)O)COC(=O)CC(SC(=N)N)C(=O)O]

Also, the present invention provides a preparation method of the corrosion inhibitor for the soft water circulation heating and cooling system, the preparation method comprising steps of:

(S1) under nitrogen protection and room temperature, evenly mixing 1,2,3,4,5-pentapentanol, 2,2-dimethylolpropionic acid, and p-toluene sulfonic acid, heating to 140-150° C., performing reaction for 3-5 h under atmospheric pressure, perform reaction for 3-5 h under vacuum conditions, and obtaining 1,2,3,4,5-penta(2,2-dimethylolpropionic acid) amyl alcohol ester with a chemical formula of $C_5H_7O_5[COC(CH_3)(CH_2OH)_2]_5$, wherein the step of (S1) is expressed by a formula of (Formula 2)

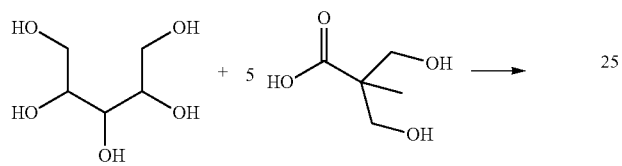 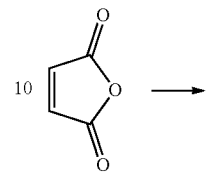

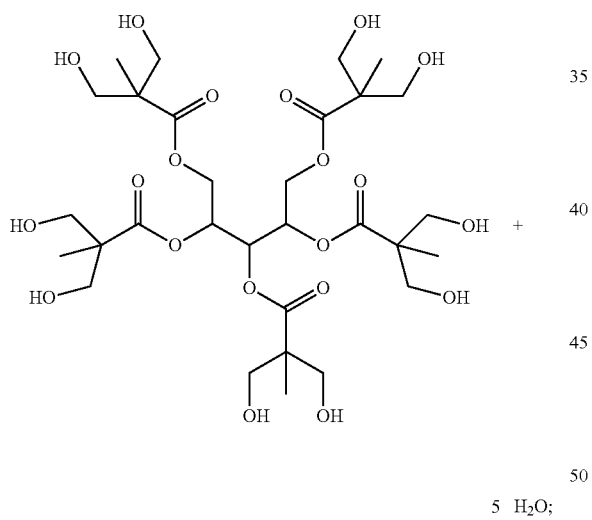

5 $H_2O$;

(S2) cooling the 1,2,3,4,5-penta(2,2-dimethylolpropionic acid) amyl alcohol ester obtained by the step of (S1) to 70-80° C., adding a first amount of acetic acid for dissolving, and then adding a mixture of maleic anhydride and a second amount of acetic acid, performing reaction for 3-5 h, and obtaining an acetic acid solution containing hyperbranched macromolecules with carboxyl-terminated pentapentanol core, wherein a chemical formula of the hyperbranched macromolecules with carboxyl-terminated pentapentanol core is $C_5H_7O_5[COC(CH_3)(CH_2OCOCH=CHCOOH)_2]_5$, the step of (S2) is expressed by a formula of (Formula 3)

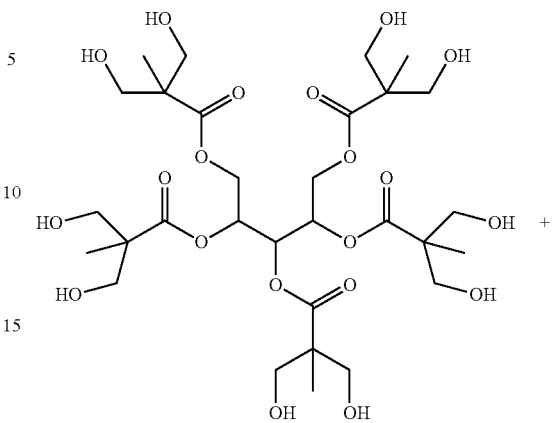

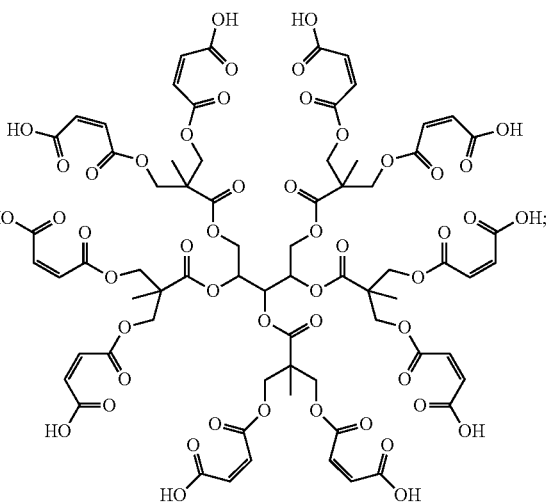

and (S3) cooling the acetic acid solution containing hyperbranched macromolecules with carboxyl-terminated pentapentanol core obtained by the step of (S2) to 40-60° C., and then adding a mixed solution of thiourea and a third amount of acetic acid, performing reaction for 3-5 h, cooling to room temperature, precipitating a solid substance, and then filtering, washing with water and drying the solid substance under vacuum in sequence, and obtaining the pentapentanol core hyperbranched macromolecule functionalized by isothiourea and carboxyl, wherein the step of (S3) is expressed by a formula of

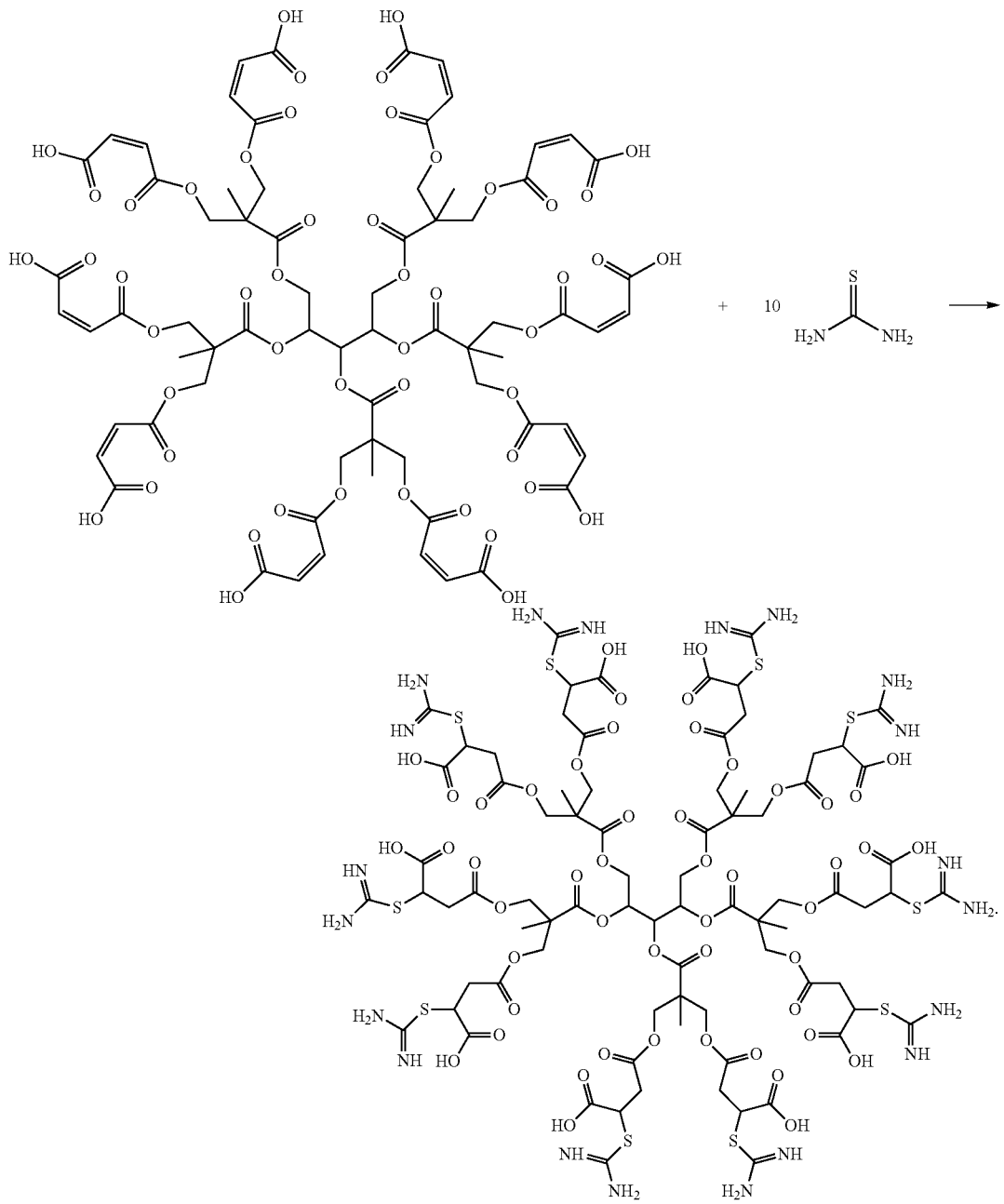

(Formula 4)

Preferably, the 1,2,3,4,5-pentapentanol is xylitol (D-pentapentanol), DL-arabinol, D(+)-arabinol or L(−)-arabinol.

Preferably, a molar ratio of 1,2,3,4,5-pentapentanol, 2,2-dimethylolpropionic acid, maleic anhydride, and thiourea is in a range of 1:(5.0-5.1):(10.0-10.2):(10.0-10.5), and more preferably, 1:5.0:10.0:10.0.

The present invention provides a corrosion inhibitor for a soft water circulation heating and cooling system, which is pentapentanol core hyperbranched macromolecule functionalized by isothiourea and carboxyl. Compared with the prior art, the corrosion inhibitor provided by the present invention has advantages as follows: (1) it does not contain phosphorus, reducing the risk of water eutrophication; (2) it is biodegradable and environmentally friendly, and has no harm to the water body; (3) it does not contain chromate, nitrite and other toxic corrosion inhibitors suitable for soft water, it is safe to use and is conducive to environmental protection; it does not contain expensive corrosion inhibitors such as molybdate and tungstate suitable for soft water, which makes the price of the compound formula low and reduces the processing cost; it does not contain silicate, and has no need to consider the danger of silica scaling in the system; (4) while being applied to the soft water circulation heating and cooling system, it is able to be adsorbed on the surface of the device without calcium supplement, alkali supplement and pH adjustment, which achieves the purpose of corrosion inhibition, simplifies operation and management, improves the stability and safety of the system, and is able to effectively suppress corrosion of devices in the circulation heating and cooling system which uses soft water as circulating water, reduce the corrosion rate of devices and significantly improve the reuse rate of circulating water.

The preparation method of pentapentanol core hyperbranched macromolecule functionalized by isothiourea and carboxyl provided by the present invention is simple in process, easy to obtain raw materials, and easy to industrialize.

DETAILED DESCRIPTION OF THE PREFERRED EMBODIMENT

A corrosion inhibitor for a soft water circulation heating and cooling system and a preparation method thereof provided by the present invention are described detailedly in combination with embodiments as follows, but these embodiments are unable to be understood as limiting the protective scope of the present invention.

The corrosion inhibition performance evaluation methods of the corrosion inhibitors in the following embodiments are carried out in accordance with the National Standard of the People's Republic of China "GB/T18175-2014, Determination of Corrosion Inhibition Performance of Water Treatment Agents by Rotating Hanging Piece Method". Experimental instrument: RCC-II Rotating hanging piece corrosion tester; experimental conditions: temperature is in a range of 45 to 80° C., a rotational speed is 75 r/min, no pre-film hanging piece is provided, time is 72 hours, carbon steel test piece: 20# carbon steel with a size of 50 mm×25 mm×2 mm. Do blank experiments at the same time.

First Control Example

Commercially available hydroxyethylene diphosphonic acid which is abbreviated as HEDP and has a solid content of 50%.

Second Control Example

Commercially available 2-phosphate-1,2,4-tricarboxylic acid butane which is abbreviated as PBTCA and has a solid content of 50%.

Third Control Example

Pentaerythritol pentaisothioureidosuccinate is prepared through a method disclosed by CN 106277376 B

First Embodiment

Preparation of Pentapentanol Core Hyperbranched Macromolecule Functionalized by Isothiourea and Carboxyl At room temperature, add 15.20 g (0.10 mol) of xylitol (1,2,3,4,5-pentapentanol), 67.00 g (0.50 mol) of 2,2-dimethylolpropionic acid, and 1.00 g of p-toluene sulfonic acid to a four-necked round bottom flask with a condenser for stirring and refluxing and a thermometer and evenly stir. And then, introduce nitrogen into the four-necked round bottom flask, heat to 145° C., perform reaction for 3 h under atmospheric pressure, perform reaction for 4 h under vacuum conditions, and obtain a sticky substance. And then cool to 80° C., add 100 g of acetic acid for dissolving, and then add 196.00 g of acetic acid containing maleic anhydride (in which the maleic anhydride is 1.00 mol and has a mass concentration of 50%), and perform reaction for 4 h. And then cool to 55° C., add 152.00 g of acetic acid containing thiourea (in which the thiourea is 1.00 mol and has a mass concentration of 50%), and perform reaction for 5 h. And then cool to room temperature, precipitate a white substance, filter under vacuum, wash with deionized water until free of acetic acid, dry, and obtain a product, namely, the pentapentanol core hyperbranched macromolecule functionalized by isothiourea and carboxyl.

The $^{13}$CNMR (D$_2$O) spectra of the pentapentanol core hyperbranched macromolecule functionalized by isothiourea and carboxyl are 18.35, 36.54, 37.98, 42.56, 61.98, 66.03, 68.93, 69.82, 136.23, 171.49, 174.39 and 180.93 ppm.

The results of corrosion inhibition performance of the pentapentanol core hyperbranched macromolecule functionalized by isothiourea and carboxyl for carbon steel with soft circulating water are shown in Table 1. Experimental conditions are as follows: the soft circulating water has a pH value of 5.6 and an electrical conductivity of 0.96 μs/cm, temperature is 45° C.

TABLE 1

The results of corrosion inhibition performance of the pentapentanol core hyperbranched macromolecule functionalized by isothiourea and carboxyl for carbon steel with soft circulating water

| Serial No. | Reagent | Concentration of reagent (dried) (mg·L$^{-1}$) | Annual corrosion rate (mm·a$^{-1}$) | Corrosion inhibition rate (%) |
|---|---|---|---|---|
| Blank case | — | 0 | 1.8632 | — |
| First Embodiment | Pentapentanol core hyperbranched macromolecule functionalized by isothiourea and carboxyl | 10 | 0.1992 | 89.30 |
| | | 20 | 0.0418 | 97.75 |
| | | 30 | 0.0292 | 98.43 |
| First Control Example | HEDP | 30 | 1.8021 | 3.28 |
| | | 40 | 1.6935 | 9.11 |
| Second Control Example | PBTCA | 30 | 1.4927 | 3.78 |
| | | 40 | 1.5716 | 19.89 |
| Third Control Example | Pentaerythritol pentaisothioureido-succinate | 20 | 0.5109 | 72.58 |
| | | 30 | 0.0957 | 94.86 |
| | | 40 | 0.0602 | 96.77 |

Second Embodiment

Preparation of Pentapentanol Core Hyperbranched Macromolecule Functionalized by Isothiourea and Carboxyl At room temperature, add 15.20 g (0.10 mol) of DL-Arabitol (1,2,3,4,5-pentapentanol), 67.00 g (0.50 mol) of 2,2-dimethylolpropionic acid, and 1.00 g of p-toluene sulfonic acid to a four-necked round bottom flask with a condenser for stirring and refluxing and a thermometer and evenly stir. And then, introduce nitrogen into the four-necked round bottom flask, heat to 140° C., perform reaction for 5 h under atmospheric pressure, perform reaction for 5 h under vacuum conditions, and obtain a sticky substance. And then cool to 80° C., add 100 g of glacial acetic acid for dissolving, and then add 197.96 g of acetic acid containing maleic anhydride (in which the maleic anhydride is 1.01 mol and has a mass concentration of 50%), and perform reaction for 4 h. And then cool to 55° C., add 155.04 g of acetic acid containing maleic anhydride (in which the thiourea is 1.02 mol and has a mass concentration of 50%), and perform reaction for 5 h. And then cool to room temperature, precipitate a white substance, filter under vacuum, wash with deionized water until free of acetic acid, dry, and obtain a product, namely, the pentapentanol core hyperbranched macromolecule functionalized by isothiourea and carboxyl.

The $^{13}$CNMR (D$_2$O) spectra of the pentapentanol core hyperbranched macromolecule functionalized by isothiourea and carboxyl are 18.29, 36.11, 38.36, 42.52, 61.76, 66.11, 68.94, 69.93, 136.21, 171.45, 175.12 and 179.68 ppm.

The results of corrosion inhibition performance of the pentapentanol core hyperbranched macromolecule functionalized by isothiourea and carboxyl for carbon steel with soft circulating water are shown in Table 2. Experimental conditions are as follows: the soft circulating water has a pH value of 5.6 and an electrical conductivity of 0.96 μs/cm, temperature is 80° C.

TABLE 2

The results of corrosion inhibition performance of the pentapentanol core hyperbranched macromolecule functionalized by isourea and carboxyl for carbon steel with soft circulating water

| Serial No. | Reagent | Concentration of reagent (dried) (mg · L$^{-1}$) | Annual corrosion rate (mm · a$^{-1}$) | Corrosion inhibition rate (%) |
|---|---|---|---|---|
| Blank case | — | 0 | 1.9002 | — |
| Second Embodiment | Pentapentanol core hyperbranched macromolecule functionalized by isothiourea and carboxyl | 20 | 0.0519 | 97.27 |
| | | 30 | 0.0306 | 98.39 |
| First Control Example | HEDP | 30 | 1.9013 | −0.11% |
| | | 40 | 1.7619 | 7.27 |
| Second Control Example | PBTCA | 30 | 1.7901 | 5.79 |
| | | 40 | 1.7226 | 9.34 |
| Third Control Example | Pentaerythritol pentaisothioureido-succinate | 30 | 0.2125 | 88.82 |
| | | 40 | 0.1602 | 91.57 |
| | | 50 | 0.0712 | 96.25 |
| Corrosion rate of carbon steel specified in design specification of industrial circulating cooling water treatment GB50050-2007 | | | ≤0.075 | — |

The experimental results in Table 1 and Table 2 show that for soft water treatment systems, the traditional water treatment corrosion inhibitor hydroxyethylene diphosphonic acid (HEDP), 2-phosphate-1,2,4-tricarboxylic acid butane (PBTCA) basically has no corrosion inhibition effect on the corrosion of carbon steel. The pentapentanol core hyperbranched macromolecule functionalized by isothiourea and carboxyl provided by the present invention has better corrosion inhibition performance for carbon steel when the dosage (20 mg·L$^{-1}$) is less; the corrosion rate of carbon steel is lower than the national standard of 0.075 mm·a$^{-1}$, and the corrosion inhibition performance is also better than that of the small molecule corrosion inhibitor pentaerythritol pentaisothioureidosuccinate disclosed in the patent CN 106277376 B.

It can be seen from the above embodiments that the pentapentanol core hyperbranched macromolecule functionalized by isothiourea and carboxyl provided by the present invention has a good corrosion inhibition effect on the circulating heating and cooling water treatment system using soft water as the water source, and is a kind of phosphorus-free, biodegradable, and environmentally friendly corrosion inhibitor.

The above are only preferred embodiments of the present invention, it should be noted that for those skilled in the art, without departing from the principles of the present invention, many improvements and modifications can be made, and these improvements and modifications should also be considered as the protective scope of the present invention.

What is claimed is:

1. A corrosion inhibitor for a soft water circulation heating and cooling system, wherein the corrosion inhibitor is pentapentanol core hyperbranched macromolecule functionalized by isothiourea and carboxyl, which has a chemical formula of $C_5H_7O_5\{COC(CH_3)[CH_2OCOCH_2CH(COOH)SC(NH)NH_2]_2\}_5$, and a structural formula of:

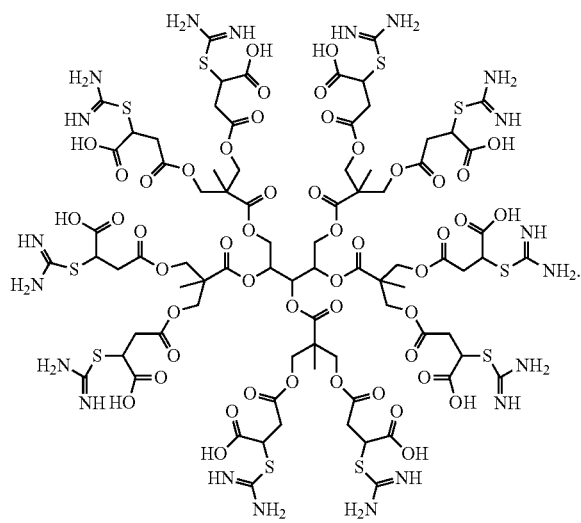

2. A preparation method of the corrosion inhibitor for the soft water circulation heating and cooling system as recited in claim 1, the preparation method comprising steps of:
   (S1) under nitrogen protection and room temperature, evenly mixing 1,2,3,4,5-pentapentanol, 2,2-dimethylolpropionic acid, and p-toluene sulfonic acid, heating to 140-150° C., performing reaction for 3-5 h under atmospheric pressure, perform reaction for 3-5 h under vacuum conditions, and obtaining 1,2,3,4,5-penta(2,2-dimethylolpropionic acid) amyl alcohol ester;
   (S2) cooling the 1,2,3,4,5-penta(2,2-dimethylolpropionic acid) amyl alcohol ester obtained by the step of (S1) to 70-80° C., adding a first amount of acetic acid for dissolving, and then adding a mixture of maleic anhydride and a second amount of acetic acid, performing reaction for 3-5 h, and obtaining an acetic acid solution containing hyperbranched macromolecules with carboxyl-terminated pentapentanol core, wherein a chemical formula of the hyperbranched macromolecules with carboxyl-terminated pentapentanol core is $C_5H_7O_5[COC(CH_3)(CH_2OCOCH=CHCOOH)_2]_5$; and
   (S3) cooling the acetic acid solution containing hyperbranched macromolecules with carboxyl-terminated pentapentanol core obtained by the step of (S2) to 40-60° C., and then adding a mixed solution of thiourea and a third amount of acetic acid, performing reaction for 3-5 h, cooling to room temperature, precipitating a solid substance, and then filtering, washing with water and drying the solid substance under vacuum in sequence, and obtaining the pentapentanol core hyperbranched macromolecule functionalized by isothiourea and carboxyl.

3. The preparation method, as recited in claim 2, wherein the 1,2,3,4,5-pentapentanol is xylitol (D-pentapentanol), DL-arabinol, D(+)-arabinol or L(−)-arabinol.

4. The preparation method, as recited in claim 2, wherein a molar ratio of 1,2,3,4,5-pentapentanol, 2,2-dimethylolpropionic acid, maleic anhydride, and thiourea is in a range of 1:(5.0-5.1):(10.0-10.2):(10.0-10.5).

5. The preparation method, as recited in claim 3, wherein a molar ratio of 1,2,3,4,5-pentapentanol, 2,2-dimethylolpropionic acid, maleic anhydride, and thiourea is in a range of 1:(5.0-5.1):(10.0-10.2):(10.0-10.5).

* * * * *